United States Patent [19]

Sapko et al.

[11] Patent Number: 4,793,710
[45] Date of Patent: Dec. 27, 1988

[54] METHOD AND APPARATUS FOR MEASURING SURFACE DENSITY OF EXPLOSIVE AND INERT DUST IN STRATIFIED LAYERS

[75] Inventors: Michael J. Sapko, Finleyville; Henry E. Perlee, Bethel Park, both of Pa.

[73] Assignee: The United States of America as represented by the Secretary of the Interior, Washington, D.C.

[21] Appl. No.: 59,892

[22] Filed: Jun. 9, 1987

[51] Int. Cl.$^4$ .................................................. G01N 21/55
[52] U.S. Cl. .................................... 356/446; 356/448
[58] Field of Search ................. 356/445, 446, 447, 448

[56] References Cited

U.S. PATENT DOCUMENTS 1,894,808  1/1933  Witte ..................................... 356/448
2,895,809  1/1933  Witte ..................................... 356/448
4,566,798  1/1986  Haas ..................................... 356/448

OTHER PUBLICATIONS

Arkin et al., *Statistical Methods*, fifth edition, College Outline Series, Barnes & Noble, New York, ©1970, pp. 100–101.

Primary Examiner—Richard A. Rosenberger
Attorney, Agent, or Firm—E. Philip Koltos

[57] ABSTRACT

A method for determining the surface density of coal dust on top of rock dust or rock dust on top of coal dust is disclosed which comprises directing a light source at either a coal or rock dust layer overlaying a substratum of the other, detecting the amount of light reflected from the deposit, generating a signal from the reflected light which is converted into a normalized output ($\overline{V}$), and calculating the surface density from the normalized output. The surface density $S_c$ of coal dust on top of rock dust is calculated according to the equation:

$$S_c = 1/-a_c \ln(\overline{V})$$

wherein $a_c$ is a constant for the coal dust particles, and the surface density $S_r$ of rock dust on top of coal dust is determined by the equation:

$$S_r = \frac{1}{-a_r} \ln(1 - \overline{V})$$

wherein $a_r$ is a constant based on the properties of the rock dust particles. An apparatus is also disclosed for carrying out the method of the present invention.

11 Claims, 2 Drawing Sheets

METHOD AND APPARATUS FOR MEASURING SURFACE DENSITY OF EXPLOSIVE AND INERT DUST IN STRATIFIED LAYERS

FIELD OF THE INVENTION

The present invention relates generally to a method and apparatus for determining the mass surface density of explosive and inert dusts in stratified explosive and inert dust layers, and more particularly to an optical method for measuring explosive levels of coal and inert levels of rock dust in underground mines.

BACKGROUND OF THE INVENTION

In coal mining, dust is produced at the face, along conveyors, at loading points, at belt transfer points, in drilling operations, and by the normal movement of men and machines. Although the coarse dust particles settle rapidly, the fine particles remain airborne and are often transported by the ventilating air for relatively long distances into the returns before settling. During mining, coal dust is carried in the air stream and deposited almost continuously, whereas rock dust is applied and deposited intermittently. This results in stratified layers of dust on the ribs, roof and floor, rather than homogeneous mixtures of coal and rock dust. These deposited particles include a reactive fraction called "float coal dust" which consist of particles of coal that when dry pass through a no. 200 sieve (74 micrometers).

The degree of explosion hazard posed by this reactive dust is related to the concentration of float coal dust lying on top of a properly rock dusted substratum. Ignition of a relatively small amount of methane-air or dust-air mixture can start a small explosion that entrails coal dust from the mine surfaces, disperses it into the air and ignites it. In the U.S. the coal dust deposits are usually protected by generalized rock dusting. The incombustible amount of dust is required by law to be 80 percent in a return airway. In the presence of methane, the amount of inert rock dust needed is increased by 1 percent for each 0.4% methane in the ventilating air. However, if a fresh layer of coal dust greater than about 50 mg/l is deposited on top of a properly (80% rock dust) rock dusted substratum, this new layer can be skimmed off by a relatively weak methane-air explosion. Such a hazardous coal dust layer is only 0.124 millimeter thick.

Mine operators, in order to comply with the law and provide protection against such an occurrence, place a trickle rock duster in the returns to periodically liberate rock dust into the ventilating air. Other methods include periodic raking of the entry or generalized re-rock dusting of the entire entry. Presently, very little actual data are available regarding float dust deposition rates in U.S. mines and operators are forced to rely on visual observations to determine the severity of the float-dust deposits. Therefore, the frequency with which new rock dust should be dispersed or when raking should be done to protect the new coal dust deposit is unknown. The result is that the current rock dusting practices cause some mine operators to rock dust excessively in some areas at the expense of others.

There are disclosed in the prior art several devices for detecting particle concentrations or thickness of particle layers. For example, U.S. Pat. No. 4,420,256 (Fladda et al.) discloses a measuring apparatus for obtaining concentration and/or particle diameter of dust particles in a flowing medium. This apparatus obtains these measurements by illuminating the flowing particles with light in a direction different from the direction of flow.

In U.S. Pat. No. 3,647,301 (Sturzinger), a system is disclosed for determining a layer thickness in the accumulation of pulverulent, granular or flaky goods. The system monitors reflected light from the good deposited on a moving surface and uses an optical system to measure the layer thickness of the accumulation.

In U.S. Pat. No. 4,474,472 (Winter), a measuring system is disclosed for detecting particles in a gas flow, such as toner particles which might be found on a photoconductor drum in a non-mechanical fast printer. This system provides a light source together with a light detector so that the detected light as influenced by the particles controls a connected evaluating circuit.

In U.S. Pat. No. 3,564,263 (Shaw) and 3,810,617 (Steinberg), apparatuses for determining the concentration of particles in a fluid stream are disclosed. The apparatuses use light rays which are directed through the stream.

A method for determining the inert content in coal dust/inert dust mixtures has been disclosed in a co-pending application (U.S. Ser. No. 943,347, filed Dec. 19, 1986 which measures the concentration of inert dust in a homogenous mixture of coal dust and inert rock dust. That method thus involves taking samples of coal dust and rock dust and combining the two into a mixture before a determination of concentration is made and does not measure surface densities of layers of dust while settled in various places in an underground mine.

The prior art thus does not disclose a method by which the surface density of stratified layers of explosive float coal dust and the inert rock dust deposited at different locations in an underground mine can be measured quickly, safely and accurately.

SUMMARY OF THE INVENTION

In accordance with the present invention, a method and apparatus is provided for determining the surface density of explosive coal dust on top of a rock dust substream or the surface density of inert rock dust on top of coal dust in underground mines using a dust accumulation meter. The levels of these dusts are determined by an in situ measurement of the optical relectivity of light from the combined coal dust/rock dust diffuse reflecting surface. In order to measure this reflectivity, a light source is directed onto the dust mixture, and the reflected light is monitored by a detector which generates a signal proportional to the reflected light received. This signal output is used to determine the surface density of a dust deposit. For a determination of the amount of coal dust on top of rock dust, or a white reflecting surface, the surface density is approximated by the equation $$S_c = 1/-a_c ln(\overline{V})$$

where $S_c$ is the surface density of coal dust in mg/cm$^2$, $\overline{V}$ is the normalized signal output, and $a_c$ is a constant which is a function of the coal dust particle diameter $D_c$ in centimeters and the coal dust density $l_c$ as g/cm$^3$, and which is expressed as follows:

$$a_c = \frac{k}{l_c D_c}$$

The normalized output $\overline{V}$ is proportional to the light intensity as follows:

$$\tilde{V} = I/I_o$$

where I/Io is the ratio of the reflected light to that reflected from the pure rock dust on a white surface. The amount of light reflected from a layer of rock dust will decrease with the accumulation of a superficial layer of float coal dust. As the surface reflectivity decreases, the measured surface density $S_c$ of the coal dust will thus increase.

In order to determine the surface density of rock dust on top of a coal dust substratum, or on top of a black non-reflecting surface, the surface density $S_r$ (in mg/cm$^2$) of the rock dust is approximated by the equation $$S_r = \frac{1}{-a_r} \ln(1 - \tilde{V})$$

where $a_r$ is a constant expressed as a function of rock dust particle diameter $D_r$ in centimeters and of rock dust particle density $l_r$ in g/cm$^3$, and which follows the relationship:

$$a_r = \frac{k}{l_r D_r}$$

and where $\tilde{V}$ is the normalized output. In this case, the amount of light reflected from the coal dust layer will increase with the increasing accumulation of white rock dust particles.

In use, the apparatus must be initially calibrated to give readings for pure coal dust and for pure rock dust. Using a calibration curve based on the particular rock dust or coal dust being used, a surface density corresponding to a "saturation point" is determined. Typically 14 mg/cm$^2$ for rock dust on coal dust and 7 mg/cm$^2$ for coal dust on rock dust are the levels corresponding to the saturation density.

Once the saturation surface densities are known, normalized output $\tilde{V}$ can be calculated from the following equations:

$$\tilde{V}_{sat,cd} = e^{-a_c S_{csat}}$$

for coal dust on rock dust, and $$\tilde{V}_{sat,rd} = 1 - e^{-a_r S_{rsat}}$$

for rock dust on coal dust.

The detector circuitry is then adjusted so that the output of the normalizing circuit will read $\tilde{V}_{sat,cd}$ for a pure coal dust sample and $\tilde{V}_{sat,rd}$ when a pure rock dust sample is tested.

Thus, with knowledge of the surface densities of explosive and inert coal dust in the particular area monitored, the lower explosive limit for the coal, and the background methane concentration, the method and apparatus of the present invention can provide important safety information with regard to the hazards presented by explosive coal dust in underground mining areas. The present invention provides a quick and reliable method for determining in situ the surface densities of coal and rock dust which is deposited at many different places in underground mines, and this determination can be accomplished safely, conveniently and accurately as well.

Other features and advantages of the present invention will be stated in or apparent from a detailed description of presently preferred embodiments of the invention found hereinbelow.

DETAILED DESCRIPTION OF THE PREFERRED EMBODIMENTS

Figure 1:
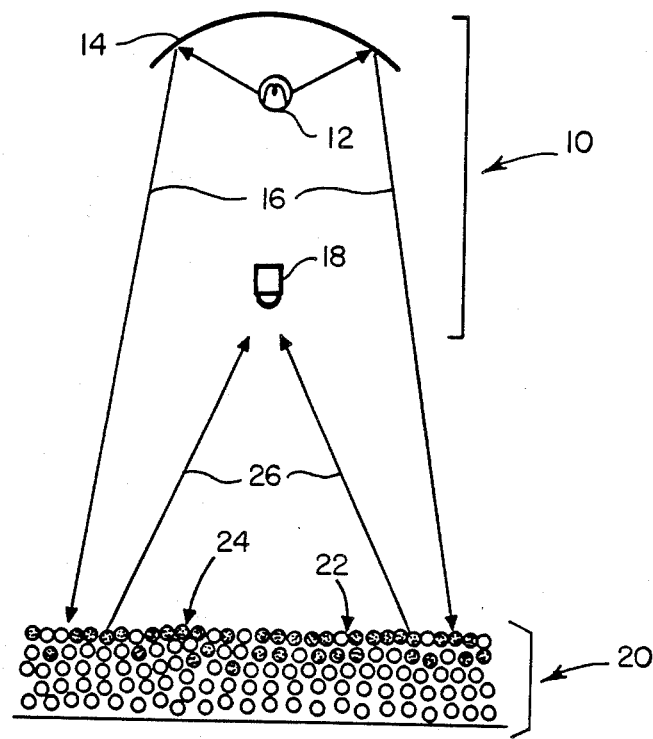
FIG. 1 is a schematic view of the dust accumulation meter of the present invention.

The method of the present invention is based upon the measurement of optical reflectivity of a surface which is made up of a mixture of dark coal dust particles and light rock dust particles. The amount of light reflected from this surface will decrease with increasing surface accumulation of coal dust, and will increase with increasing accumulation of rock dust. The amount of light reflected from a pure coal dust surface and from a pure rock dust surface can be utilized in calibrating the normalized output signal from a light detector so that the surface density of rock dust on coal dust or the surface density of coal dust on rock dust can be determined.

According to the method of the present invention, the surface densities of coal and rock dust can be determined by a measurement of optical reflectivity of light from the diffuse reflecting surface where the dusts are deposited. In order to measure reflectivity, there is provided a light source directed onto the dust surface, and the reflected light from the surface is received by light detecting means. The light source and the light detecting means can be employed in a single device or meter which measures the amount of reflected light from the dust deposit. The reflected light generates a signal proportional to the amount of reflected light received, and this signal output is employed to determine the surface density of coal dust or rock dust in a dust deposit.

For the determination of the amount of coal dust on top of rock dust, or any white reflecting surface, the signal output can be used to establish the surface density of the coal dust. The coal dust surface density is approximated by the equation $$S_c = 1/a_c \ln(\tilde{V}) \qquad (1)$$

wherein $S_c$ equals the surface density of the coal dust in mg/cm$^2$, $\tilde{V}$ is the normalized signal output, and $a_c$ is a constant which is a function of the coal dust particle diameter $D_c$ (in centimeters) and the coal dust density lc (in g/cm$^3$), and which is expressed by the equation $$a_c = \frac{k}{l_c D_c} \qquad (2)$$

The normalized signal output $\tilde{V}$ will be proportional to the light intensity as follows:

$$\tilde{V} = I/I_o \qquad (3)$$

where I/Io is the ratio of reflected light to that reflected from the pure rock dust on a white surface. The amount of light reflected from a layer of rock dust will decrease with the accumulation of float coal dust. As the surface reflectivity decreases, the measured surface density $S_c$ of the coal dust will thus increase.

For the determination of the amount of rock dust on top of coal dust, or on top of a black, non-reflecting surface, the surface density of the rock dust is approximated by the equation $$S_r = \frac{1}{-a_r} \ln(1 - \overline{V}) \qquad (4)$$

wherein $S_r$ equals the surface density of the coal dust in mg/cm$^2$, $\overline{V}$ is the normalized signal output, and $a_r$ is a constant expressed as a function of the rock dust particle diameter $D_r$ (in cm) and the rock dust particle density $l_r$ (in g/cm$^3$) and which follows the relationship:

$$a_r = \frac{k}{l_r D_r} \qquad (5)$$

In this case, the amount of light reflected from the coal dust layer will increase with increasing amounts of light rock dust particles, and the measured surface density of the rock dust, $S_r$, will increase with increasing reflectivity.

A dust accumulation meter apparatus 10 for carrying out the method of the present invention is depicted schematically in FIG. 1. As shown, the dust meter includes a light source 12, reflecting means 14 for directing incident light rays 10 towards the surface 20 being sampled. The surface will be comprised generally of light rock dust particles 22 and dark coal dust particles 24. The light from source 12 directed onto the dust particles will be reflected from the surface 20, and the reflected light rays 26 are detected by detector means 18.

Figure 2:
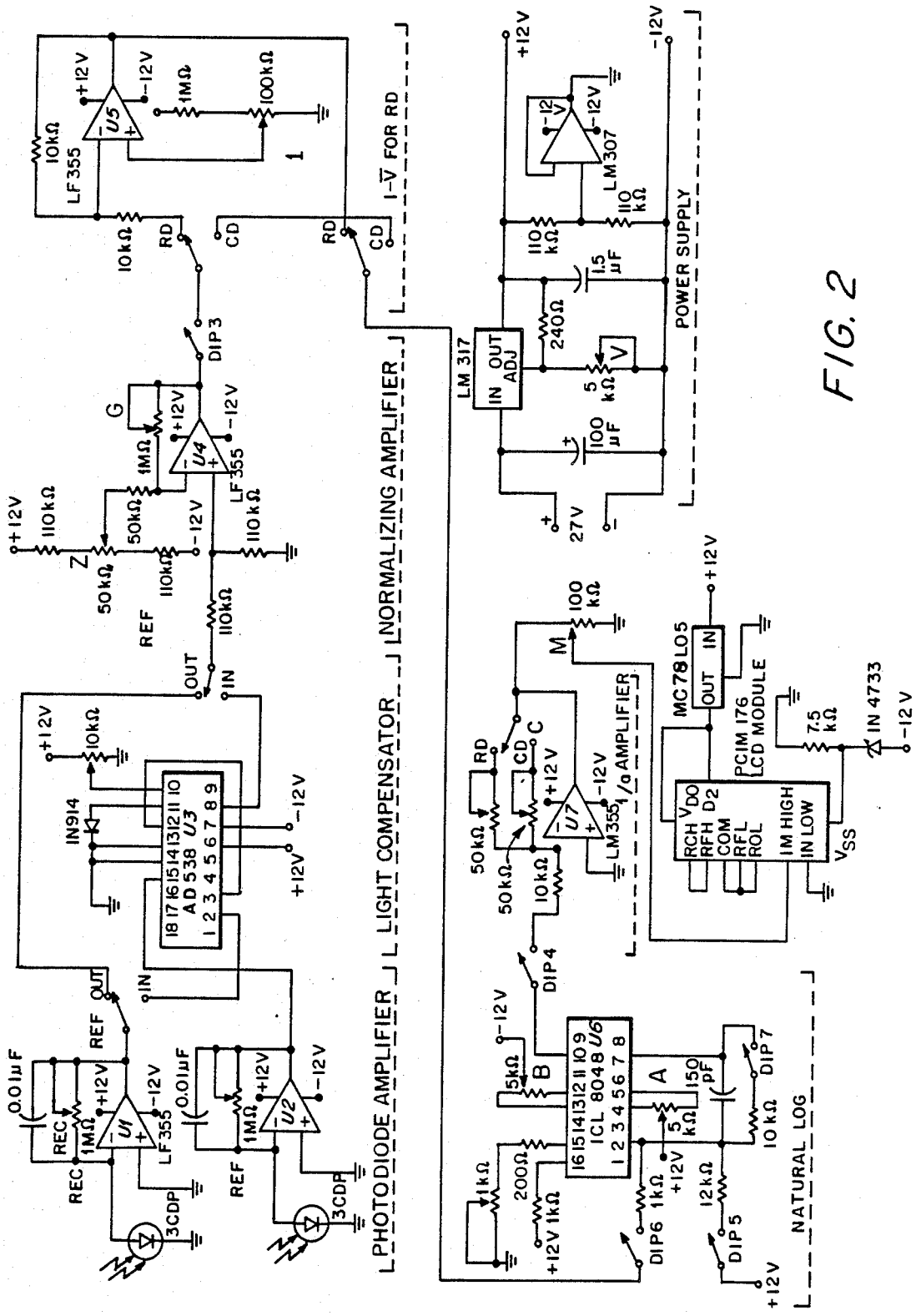
FIG. 2 is a schematic electrical diagram of the dust accumulation meter of the present invention.

Circuitry for the dust accumulation meter suitable for use in the present invention is depicted schematically in FIG. 2. The circuit operates on 27 VDC. The LM317 regulator is adjusted by the 5K ohm potentiometer, "$\overline{V}$", to provide a 24 VDC output. The voltage follower U7 determines the reference ground for the ±12 $\overline{V}$ supply powers all integrated circuits and the liquid crystal display. Both photo diodes are connected to op-amps, U1 and U2, which are configured as amplifiers.

The 1 meg pots ("Rec" and "Ref") adjust the gain and the 0.01 f capacitor helps eliminate noise. The light compensation circuit, U3, is an Analog Devices AD538 configured as an analog divider which divides the receiver photodiode voltage by the preference photodiode voltage. The 10k ohm potentiometer to pin 10 of AD558 provides the scaling factor of this ratio. The normalizing circuit consists of op-amp U4, configured as a 2-input amplifier. Potentiometer "G" provides the gain and potentiometer "Z" is adjusted to provide a zero volt output with a pure coal dust sample. Amplifier U5, produces $(1-\overline{V})$ which is needed for the rock dust equation, Equation 4, above. Pot "1" generated 1 in Equation 4 and U6 is a log chip designed to take the natural log of the input. Basically the circuit is designed so that $\overline{V}_{out} = k \ln(\overline{V}_{in})$. The 1k ohm pot attached to pin 15 of ICL8048 is adjusted so that k=1. The chip U7, multiplies the log term by the 1/a constant (Equation 1 above) needed to find the surface density. Potentiometer C adjusts for the 1/$a_c$ constant (Equation 1 above) and the pot marked $R_d$ adjusts for the 1/$a_r$ constant. The output at this point is equal to the negative surface density but since it is connected to "IN LO" on the LCD module and "IN HI" is grounded, a positive result will be shown on the CCD. The power supply for the LCD module consists of a 5 V regulator (MC78L05) and a 5.1 V zener diode (IN433). These are used to provide −13 VDC for the module.

For the initial circuit setup, the following steps should be undertaken:

(a) With power supplied, adjust pct $\overline{V}$=24 vdc between negative supply and pin 2 of the LM317 regulator. Set the dip switches in the following manner: dip 1 through 6: off and dip 7: on;

(b) Adjust pot "A" until the voltage at the test point on dip 7 is equal to zero volts;

(c) Turn dip 7 off and turn dip 5 on, adjust pot "B" for zero volts at the test point on dip 4. The log chip, U6, is now zeroed;

(d) Calibrate the divider chip, U3, if necessary by adjusting the 10k ohm pot at pin 10 so there is 1 V at pin of 10 of U3; and (e) Turn dip 5 off and dip 3, 4, 6 on. The "REF" switch is in the "IN" position and the select switch is in the "CD" position. These are the switch setting for normal operation.

Before operation, the circuit must be calibrated to give the correct readings for pure coal dust and rock dust. Using calibration curves for the particular rock dust and coal dust being used, a surface density which corresponds to a "saturation point" is determined. This is the point at which maximum reflectance, in the case of rock dust or minimum reflectance, in the case of coal dust is achieved. Typically these saturation surface densities are about 14 mg/cm$^2$ for rock dust on coal dust ($S_r$sat) and 7 mg/m$^2$ for coal dust on rock dust ($S_c$sat).

Once these "saturation densities" are known, the corresponding $\overline{V}$'s can be calculated from the following equations:

$$\overline{V}_{sat,cd} = e^{-a_c S_c sat} \qquad (6)$$

wherein $a_c$ is as described above, for coal dust on rock dust, and $$\overline{V}_{sat,rd} = 1 - e^{-a_r S_r sat} \qquad (7)$$

wherein $a_r$ is as described above, for rock dust on coal dust.

The gains of the two photodiode amps and the "gain" and "zero" of the normalizing circuit must be adjusted so that the output of the normalizing circuit, the test point on dip 3, will read $\overline{V}$sat,rd and $\overline{V}$sat,cd when the corresponding pure sample is tested. On the normalizing circuit, the "Z" pot can be used to adjust for a correct pure coal dust reading, and the "G" pot can be used to adjust for a correct pure rock dust reading.

To complete the calibration for the rest of the circuit, a sample equivalent to pure coal dust is tested by the meter add $\overline{V}$ is measured (test point at dip 3). The select switch is placed in the "RD" position and pot "1" is adjusted until the voltage at the test point at dip 3 is equal to $(1-\overline{V})$. The select switch is then placed back in the "CD" position and the voltage is measured at the test point at dip 4. The 1k ohm pot on pin 15 of ICL8048 is adjusted until this voltage is equal to $-\ln(\overline{V})$. The "C" pot is then adjusted so that the output (pin 6) of U7 is equal to 1/$a_c$ ln(V), and pot "M" is adjusted so that the LCD displays the same reading. Finally, with the select switch in "RD" position, the adjacent 50K ohm pot is adjusted until the LCD display = 1/$a_r$ ln $(1-\overline{V})$.

Once the above initial setup has been completed, it will only be necessary to adjust the "Z" and "G" pots to give the proper surface density reading on the LCD display for pure coal dust and rock dust samples ($S_c$sat and $S_r$sat) when the circuit is used.

The dust accumulation meter can thus be used to measure explosive coal dust layers or inert rock dust layers at various areas of dust deposits in an underground mine. Knowing the entry size, the lower explosive limit for the coal, and the background methane concentration, the meter can provide a quantitative measure of the float coal surface density which is proportional to the lower explosion limit for that entry.

Figure 3:
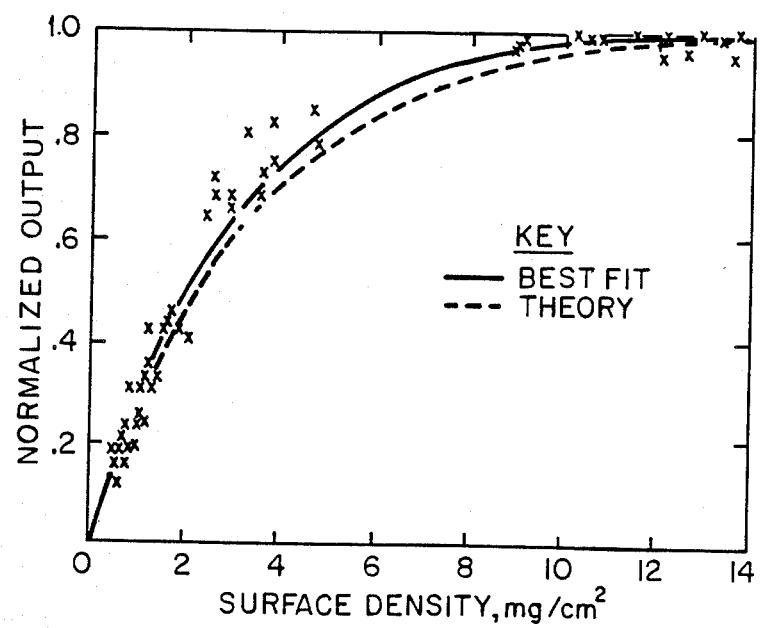
FIG. 3 is a graphical representation of a plot of density of rock dust on coal dust versus normalized output.

Testing results of the dust accumulation meter at the Lake Lynn Experimental Mine showed that actual data recorded corresponded well with the theory behind the invention. In FIG. 3 is shown the normalized meter output versus rock dust surface density in mg/cm². The output starts at 0.0 for the reflectivity of pure coal dust and rises to 1.0 with the superficial accumulation of light rock dust particles. The agreement between theory an experimental results in well established by these tests. In tests on normalized output versus coal dust surface density, similar agreement between theory and experimental results was observed. In this case the output started at 1.0 (high reflectivity) for the rock dust and decreased exponentially for the accumulation of coal dust on top of rock dust. The device used had a resolution of better than 1 mg/cm² of coal dust on rock dust, which is about 10 percent of the lower explosive limit (10 mg/cm²) for Pittsburgh Coal in the 7 by 19 foot entries.

The method and apparatus of the present invention is thus capable of detecting hazardous accumulations of float coal on rock dust as well as safe layers of rock dust on top of coal dust. With the dust accumulation meter and the method of the present invention, the mining industry will have a means of monitoring float coal deposits and will be able to provide the proper addition of rock dust so as to render the potentially explosive coal dust harmless. The present invention can also be extended to determine surface densities in other applications involving contrasting dusts, one or both of which can pose a potential health hazard. An example of another application of the present invention would be the grain industry where the dust meter could be used to monitor the accumulation of explosive grain dust.

What is claimed is:

1. A method for determining the surface density of a coal dust layer on top of a rock dust substratum comprising the steps of:
   directing a light source onto a coal and rock dust deposit;
   detecting the amount of light reflected from the dust deposit;
   generating a signal proportional to the amount of light reflected from the dust deposit;
   determining a normalized output for the signal generated;
   calibrating the normalized output to correspond to range of values from a point at which a minimum amount of light is reflected from the dust deposit to a point at which a maximum amount of light is reflected from the dust deposit; and
   calculating the surface density of the coal dust Sc from the equation:

$$S_c = 1/-a_c \ln(\widetilde{V})$$

wherein $\widetilde{V}$ is the normalized output, and $a_c$ is a constant which is a function of the coal dust particle diameter $D_c$ and of the coal dust particle density $l_c$, and which follows the relationship:

$$a_c = \frac{k}{l_c D_c}$$

wherein k is a constant.

2. A method according to claim 1 wherein surface density is measured in mg/cm², particle diameter is measured in cm, and coal dust particle density is measured in mg/cm³.

3. A method according to claim 1 wherein the calibration step includes a determination of a saturation surface density of the coal dust, $S_c$sat, which corresponds to the approximate point where the density of coal dust on top of a rock dust substratum reaches the level at which the minimum amount of light is reflected from the deposit, and a determination of normalized output from the signal generated by the light reflected from a dust deposit at its coal dust saturation surface density $S_c$sat by the equation:

$$\widetilde{V}_{sat,cd} = e^{-a_c S_c sat}$$

wherein $\widetilde{V}_{sat,cd}$ is the normalized output at the coal dust saturation surface density and $a_c$ is a constant which is a function of the coal dust particle diameter $D_c$ and the coal dust density $l_c$ and which follows the relationship:

$$a_c = \frac{k}{l_c D_c}$$

wherein k is a constant.

4. A method according to claim 3 wherein the saturation surface density of coal dust on top of a rock dust substratum is 7 mg/cm².

5. A method for determining the surface density of a rock dust layer on top of a coal dust substratum comprising the steps of:
   directing a light source onto a coal and rock dust deposit;
   detecting the amount of light reflected from the dust deposit;
   generating a signal proportional to the amount of light reflected from the dust deposit;
   determining a normalized output for the signal generated;
   calibrating the normalized output to correspond to a range of values from a point at which a minimum amount of light is reflected from the dust surface to a point at which a maximum amount of light is reflected from the dust deposit; and
   calculating the surface density of the rock dust, Sr, from the equation:

$$S_r = \frac{1}{-a_r} \ln(1 - \widetilde{V})$$

wherein $\widetilde{V}$ is the normalized output, and $a_r$ is a constant which is a function of the rock dust particle diameter $D_r$ and of the rock dust particle density $l_r$ and which follows the relationship:

$$a_r = \frac{k}{l_r D_r}$$

wherein k is a constant

6. A method according to claim 5 wherein surface density is measured in mg/cm², particle diameter is measured in cm, and rock dust particle density is measured in mg/cm³.

7. A method according to claim 5 wherein the calibration step includes a determination of a saturation surface density of the rock dust, $S_r$sat, which corresponds to the approximate point where the density of rock dust on top of a coal dust substratum reaches the level at which the maximum amount of light is reflected from the deposit, and a calculation of normalized output from the signal generated by the light reflected from a dust deposit at its rock dust saturation surface density $S_r$sat by the equation:

$$\bar{V}_{sat,rd} = 1 - e^{a_r S_r sat}$$

wherein $\bar{V}$sat,rd is the normalized output at the rock dust saturation surface density, and $a_r$ is a constant which is a function of the rock dust particle diameter $D_r$ and the coal dust density $l_c$, and which follows the relationship:

$$a_r = \frac{k}{l_r D_r}$$

wherein k is a constant.

8. A method according to claim 7 wherein the saturation surface density of rock dust on top of a coal dust substratum is 14 mg/cm².

9. An apparatus for determining the surface density of a layer of coal dust on top of rock dust or a layer of rock dust on top of coal dust comprising:
 a light source for directing light onto a coal and rock dust deposit;
 a detecting means for detecting the amount of light reflected from the dust deposit;
 means for generating a signal proportional to the amount of light reflected from the dust deposit;
 means for determining a normalized output based on the signal generated;
 means for calibrating the normalized output to correspond to a range of values from a point at which a minimum amount of light is reflected from the dust surface to a point at which a maximum amount of light is reflected from the dust surface; and
 means for calculating the surface density of coal and rock dust from the normalized output.

10. An apparatus according to claim 9 wherein the surface density $S_c$ of coal dust on a top of rock dust is determined, and wherein said surface density is calculated according to the equation:

$$S_c = 1/-a_c \ln(\bar{V})$$

wherein $\bar{V}$ the normalized output, and $a_c$ is a constant which is a function of the coal dust particle diameter $D_c$ and of the coal dust particle density $l_c$, and which follows the relationship:

$$a_c = \frac{k}{l_c D_c}$$

wherein k is a constant.

11. An apparatus according to claim 9 wherein the surface density $S_r$ of rock dust on top of coal dust is determined, and wherein said surface density is calculated according to the equation:

$$S_r = \frac{1}{-a_r} \ln(1 - \bar{V})$$

wherein $\bar{V}$ is the normalized output, and $a_r$ is a constant which is a function of the rock dust particle diameter $D_r$ and of the rock dust particle density $l_r$, and which follows the relationship:

$$a_r = \frac{k}{l_r D_r}$$

wherein k is a constant.

* * * * *